(12) United States Patent
Hu et al.

(10) Patent No.: US 10,703,734 B2
(45) Date of Patent: Jul. 7, 2020

(54) 3-ARYL-BENZOFURANONE COMPOUND AND COMPOSITION FORMED THEREFROM

(71) Applicant: EUTEC CHEMICAL CO., LTD, Taipei (TW)

(72) Inventors: Hanmin Hu, Taicang (CN); Yufeng Zeng, Taipei (TW); Fangyuan Jiang, Taicang (CN); Haitao Wei, Taicang (CN)

(73) Assignee: EUTEC CHEMICAL CO., LTD. (TW)

( * ) Notice: Subject to any disclaimer, the term of this patent is extended or adjusted under 35 U.S.C. 154(b) by 0 days.

(21) Appl. No.: 15/523,360

(22) PCT Filed: Oct. 23, 2015

(86) PCT No.: PCT/CN2015/092655
§ 371 (c)(1),
(2) Date: Apr. 28, 2017

(87) PCT Pub. No.: WO2016/066027
PCT Pub. Date: May 6, 2016

(65) Prior Publication Data
US 2017/0253574 A1    Sep. 7, 2017

(30) Foreign Application Priority Data
Oct. 31, 2014   (CN) .......................... 2014 1 0608651

(51) Int. Cl.
| | | |
|---|---|---|
| *C07D 307/83* | (2006.01) | |
| *C08K 5/1535* | (2006.01) | |
| *C08G 18/08* | (2006.01) | |
| *C08G 18/16* | (2006.01) | |
| *C08G 18/18* | (2006.01) | |
| *C08G 18/24* | (2006.01) | |
| *C08G 18/48* | (2006.01) | |
| *C08G 18/76* | (2006.01) | |
| *C08J 9/00* | (2006.01) | |
| *C08K 5/134* | (2006.01) | |
| *C08K 5/18* | (2006.01) | |
| *C08K 5/521* | (2006.01) | |
| *C08L 53/00* | (2006.01) | |
| *C08L 55/02* | (2006.01) | |
| *C08G 101/00* | (2006.01) | |

(52) U.S. Cl.
CPC ....... *C07D 307/83* (2013.01); *C08G 18/0838* (2013.01); *C08G 18/14* (2013.01); *C08G 18/165* (2013.01); *C08G 18/1808* (2013.01); *C08G 18/244* (2013.01); *C08G 18/48* (2013.01); *C08G 18/7621* (2013.01); *C08J 9/0023* (2013.01); *C08J 9/0028* (2013.01); *C08K 5/1345* (2013.01); *C08K 5/1535* (2013.01); *C08K 5/18* (2013.01); *C08K 5/521* (2013.01); *C08L 53/00* (2013.01); *C08L 55/02* (2013.01); *C08G 2101/0008* (2013.01); *C08G 2101/0083* (2013.01); *C08J 2205/06* (2013.01); *C08J 2375/08* (2013.01); *C08L 2201/08* (2013.01)

(58) Field of Classification Search
CPC ..................................................... C08K 5/1535
See application file for complete search history.

(56) References Cited

U.S. PATENT DOCUMENTS

| | | | | |
|---|---|---|---|---|
| 4,325,863 A * | 4/1982 | Hinsken | ............... | C07D 307/83 524/111 |
| 4,611,016 A | 9/1986 | Hinsken et al. | | |
| 5,516,920 A * | 5/1996 | Nesvadba | ............ | C07D 307/83 549/307 |
| 5,668,200 A * | 9/1997 | Valet | .................... | C08K 5/3492 524/100 |
| 5,834,541 A * | 11/1998 | Becker | ..................... | C08K 3/22 524/119 |
| 7,060,425 B1 * | 6/2006 | Jeganathan | .......... | C07D 307/83 430/543 |

FOREIGN PATENT DOCUMENTS

JP           62227542 A    * 10/1987

OTHER PUBLICATIONS

Machine translated English language equivalent of JP 62-227542 (1987, 2 pages).*
SIPO, First Office Action, dated Nov. 3, 2015, Application No./Patent No. 201410608651.9.
SIPO, Second Office Action, dated Nov. 17, 2015, Application No./Patent No. 201410608651.9.
SIPO, Third Office Action, dated Mar. 2, 2016, Application No./Patent No. 201410608651.9.
SIPO, Fourth Office Action, dated Aug. 29, 2016, Application No./Patent No. 201410608651.9.

* cited by examiner

*Primary Examiner* — Brieann R Johnston

(57) ABSTRACT

The present invention discloses a 3-aryl-benzofuranone compound in which $R_1$-$R_6$ in the formula are mutually independent H or $C_1$-$C_{20}$ alkyls, and $R_7$ is $C_7$-$C_{20}$ alkyl or $C_7$-$C_{20}$ mixed alkyl. The present invention also discloses a composition of 3-aryl-benzofuranone compound and the preparation method. The 3-aryl-benzofuranone compound and the composition thereof has the superiority in application due to the characteristics of less proneness to volatilize, less proneness to be extracted, higher resistance to migration and less proneness to bloom and precipitate on the surface of organic materials, and with a wide range of application, it is effective during the application.

6 Claims, No Drawings

3-ARYL-BENZOFURANONE COMPOUND AND COMPOSITION FORMED THEREFROM

FIELD

The present invention involves the composition of 3-aryl-benzofuranone compound and the application and preparation hereof, which belongs to the field of chemical materials and its application technology.

BACKGROUND

Relative to organic polymer, multiple compositions have the stabilization functions of degradation induced by oxidation, beat and/or light. Such compositions have the potentials of being applied to thermoplastic plastics such as polyolefin, heat convertible resins such as polyurethane, and coating formula. For example, one of the current problems of polyurethane foam is the proneness of yellow discoloration after a certain period of time. The yellow discoloration of the polyurethane material is not expected; the phenomenon of yellow discoloration is due to the heat and/or light induced oxidation, as well as the nitrogen oxide (Nox) induced gas fumigation.

The use of 3-aryl-benzofuranone compound as a stabilizer for organic compound is known; for example, in U.S. Pat. Nos. 4,325,863 and 4,338,244, Hinsken discloses the use of 3-aryl-benzofuranone and their dimer as stabilizers in various organic polymers such as polyolefin, polyurethane and polyester.

In U.S. Pat. Nos. 5,367,008, 5,369,159 and 5,428,162, Nesvadba discloses the preparation of 3-(alkoxypheny) benzofuranyl and 3-(aryloxyphenyl) benzofuranyl and the application as the polymer stabilizers.

The technology provides the stabilizers of many 3-aryl-benzofuranones, but these stabilizers still cannot satisfy the requirements in the high-performance application, such as shelf life, water absorption, hydrolysis susceptibility, processing stability, color property, volatility, mobility, intermiscibility and improvement of yellow discoloration and degradation induced by heat and/or light. As a result, there is still demand on more effective stabilizers of the oxygen, heat and/or light sensitive synthetic organic polymers. This invention provides a new 3-aryl-benzofuranone compound as the stabilizer of organic materials, in particular to the application to synthetic organic polymers, such as polyolefin, polyurethane, polyether polyol, coatings and other organic materials.

SUMMARY

The technical problem to be addressed in this invention provides a 3-aryl-benzofuranone compound and the composition, application and preparation hereof, in particular to the use of it as a stabilizer to synthetic organic polymer.

In order to address the above technical problems, the technical plan adopted hereof is as follows:

The characteristics of 3-aryl-benzofuranone compound lie in the possession of the structure as shown in formula (I):

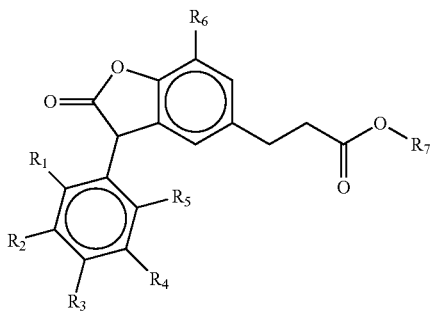

$R_1$-$R_6$ in the formula (1) are mutually independent H or $C_1$-$C_{20}$ alkyl, and $R_7$ is $C_7$-$C_{20}$ alkyl or $C_7$-$C_{20}$ mixed alkyl, and the alkyl is a straight chain and/or branched chain alkyl.

$R_1$-$R_5$ in the formula (1) are mutually independent H or $C_1$-$C_4$ alkyl, $R_6$ is $C_1$-$C_5$ alkyl, and $R_7$ is $C_7$-$C_{18}$ alkyl or $C_7$-$C_{18}$ mixed alkyl; preferably, $R_1$-$R_5$ are the mutually independent H or methyl, $R_6$ is methyl or 1,1-dimethylethyl, and $R_7$ is $C_7$-$C_{18}$ alkyl or $C_7$-$C_{18}$ mixed alkyl; further preferably, $R_1$-$R_5$ are the mutually independent H or methyl, $R_6$ is 1,1-dimethylethyl, and $R_7$ is n-octyl or 2-ethylhexyl or 6-methyl heptyl or $C_7$-$C_9$ mixed alkyl or $C_{13}$-$C_{16}$ mixed alkyl.

A composition of 3-aryl-benzofuranone compound, wherein its characteristics lie in that, comprising: Component a: organic materials prone to be degraded as induced by oxidation, heat and/or light; and Component b: at least containing 3-aryl-benzofuranone compounds as stated in formula (I).

Wherein, the organic materials are natural organic polymers, semi-synthetic organic polymers or synthetic organic polymers. The natural organic polymers are obtained from the separation from a natural source without going through further synthesis and modification; the semi-synthetic organic polymers contain at least one kind of natural organic polymer, and the natural organic polymer can be synthesized, processed and modified and or react with a monomer to form the semi-synthetic organic polymer; the synthetic organic polymers do not contain the organic polymers obtained from the separation from a natural source.

The synthetic organic polymers are polyolefin, polyether polyol or polyurethane. In addition, organic materials can also be mineral oil, grease or the organic polymers for coating. The organic polymers can be further divided into thermoplastic organic polymers and heat convertible organic polymers. The thermoplastic organic polymers can be molded into a new shape under the condition of elevated temperature (such as the temperature range of 150° C. to 340° C.).

In addition, the component b is 0.0001-10% that of component a; preferably from 0.0005%-2%; further preferably 0.001%-2%; more further preferably 0.005%-2%. The proportion of the added mass between the component b and the component a is decided according to the specific organic materials and the required degree of stability.

Further, the composition also contains component c, the component c is additive, and the additive is at least one of the following: phenolic antioxidant, phosphite ester or phosphinate ester, amine antioxidant, light stabilizer, an acid scavenger, anti-hydrolytic reagent, processing stabilizer and flame retardant. Wherein, the added mass ratio between the component c and component b is 10:1-1:30; preferably 10:1-1:20; more preferably 10:1-1:20; further preferably from 2:1-1:20; the total mass of the component c and component b is less than 50% of the mass of component a.

The above 3-arylbenzofuranone compounds are used to prepare stabilizers for organic materials susceptible to oxidative, thermal and/or light-induced degradation. Preferably, they are used as high efficient stabilizers for organic materials against oxygen, heat and/or light-induced degradation; specifically, the applications of 3-arylbenzofuranone compounds of the formula (I), are used as an efficient stabilizer for polyurethane foam including the anti-scorching agent, and used for stabilizing polyether polyols to prevent heat and/or light-induced degradation.

The composition can be used for the preparation of various shaped articles, for example, a film, pipe, profile, bottle, tank, container or fiber. Preferred articles are obtained by processes of injection molding, blow molding, compression molding, rotational molding, slush molding or extrusion molding. The article can be rigid or flexible, and preferably flexible foam produced by above mentioned composition, wherein component (a) is a polyurethane, especially, for a flexible foam composition wherein (a) is a polyurethane, component b) is formula (I) compound, and component (c) is a phenolic antioxidant, a phosphite ester or phosphinate ester, an acid scavenger, an amine antioxidant, and a flame retardant (especially an organohalogen flame retardant).

The preparation method of 3-aryl-benzofuranone is characterized by comprising the following steps: let the mixture of $C_7$-$C_{20}$ alkanol or $C_7$-$C_{20}$ alkanol react with the compound of the following formula (II) at the temperature condition of 5 to 200° C. and obtain the target product; the reaction solvent does not contain hydroxy group, and the catalytic agent for reaction is an acid catalytic agent.

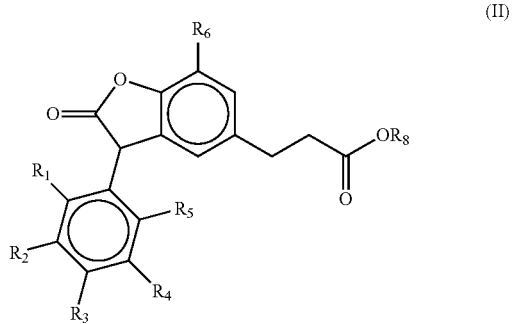

(II)

wherein the molar ratio of $C_7$-$C_{20}$ alkanols or a mixture of $C_7$-$C_{20}$ alkanols: formula (II) compound is 1-10:1, preferably 1.5-5:1, more preferably 1.5-3:1.

Furthermore, the $R_1$ to $R_6$ in the formula (II) are mutually independent H or $C_1$-$C_{20}$ alkyl, and $R_8$ is H or $C_1$-$C_6$ alkyl, and the alkyl is the straight chain and/or branched chain alkyl.

Furthermore, $R_1$-$R_5$ in the Formula (II) are mutually independent H or $C_1$-$C_4$ alkyl, $R_6$ is $C_1$-$C_5$ alkyl, and $R_8$ is H or $C_1$-$C_6$ alkyl; preferably, $R_1$ to $R_5$ are the mutually independent H or methyl. $R_6$ is methyl or 1,1-dimethylethyl, and $R_8$ is H or $C_1$-$C_6$ alkyl; further preferably, $R_1$ to $R_5$ are the mutually independent H or methyl, $R_6$ is 1,1-dimethylethyl, and $R_8$ is methyl.

The beneficial effects of the present invention are as follows: the 3-arylbenzofuranone compounds contain $C_7$-$C_{20}$ linear and/or branched alkyl chains (or the mixtures of the linear and/or branched alkyl chains substituted 3-aryl-benzofuranones) to apply and achieve the desired high compatibility, low volatility, hydrophobic, eutectic physical state and the liquid state at room temperature through the nature of 3-arylbenzofuranone or their mixtures.

In many applications, the 3-aryl-benzofuranone compound at the liquid state can provide more significant and excellent characteristics against the oxygen, heat and/or light induced degradation for the organic materials prone to be degraded as induced by oxidation, heat and/or light. In the meantime, there is also operation convenience during the application.

The composition of the 3-aryl-benzofuranone compound hereof can be in the liquid state at the room temperature; in this way, during the manufacturing and application, the liquid composition can provide better convenience to operation when applied to the organic materials. In addition, the 3-aryl-benzofuranone compounds hereof possess high compatibility in various medium such as thermoset polymers (polyurethanes) and thermoplastics (ABS, PC, PE, PET, PP, PS, SBS and the like), wax, aqueous systems (liquid hand soaps, detergents, sunscreens, fabric softeners etc. consumer products), and various kinds of liquid coatings etc. In addition, the 3-aryl-benzofuranone compound hereof has a high molecular weight, a better heat-resistance and better application than the commercially available 3-aryl-benzofuranone product; this invention also has the superiority of less proneness to volatilize, less proneness to be extracted, higher resistance to migration and less proneness to bloom and precipitate on the surface of organic materials, when compared with the commercially available Irganox HP 136 (trade name of BASF).

DETAILED DESCRIPTION

A detailed description is given on this invention according to the specific examples.

Example 1

Preparation of the mixture of methyl 3-(7-tert-butyl-3-(2,3-dimethylphenyl)-2-oxo-2,3-dihydrobenzofuran-5-yl) propanoate and methyl 3-(7-tert-butyl-3-(3,4-dimethylphenyl)-2-oxo-2,3-dihydrobenzofuran-5-yl)propanoate.

In a 1000 mL four-neck round-bottom flask equipped with mechanical stirrer, heat controller and reflux condenser, add 300 g of 1,2-dichloroethane and 118 g of methyl 3-(3-teriarybutyl-4-hydroxyphenyl) propionate, stir fully to such an extent that the methyl 3-(3-teriarybutyl-4-hydroxyphenyl) propionate is dissolved into 1,2-dichloroethane, Then add 89 g of ethanol acid (50% ethanol acid aqueous solution) and 0.9 g of para-toluenesulfonic acid monohydrate. At 85° C., heat the mixture and perform reflux for 6 hours. Subsequently, steam the 1,2-dichloroethane out under the condition of decompression. Then add 300 ml of methyl tertiary butyl ether to dissolve the crude product, and wash with water. Separate the organic phase, and remove the methyl tertiary butyl ether under the condition of decompression. Vacuum dehydrate the obtained product at 60° C., and obtain 175 g of crude product.

In another 1000 mL four-neck round-bottom flask equipped with mechanical stirrer, heat controller and reflux condenser, cool the suspension of 30 g of anhydrous aluminum chloride and 50 g of o-xylene to 0° C., and then add the above suspension to the solution in which 200 g dimethylbenzene dissolves 85 g of the above obtained crude product within 60 minutes. Subsequently, continue the stirring for 4 hours, and gradually elevate the temperature to 40° C. 16 hours thereafter, add 25 g of anhydrous aluminum chloride at 40° C., and continue stirring for 8 hours at 40° C. Add ice when cooled to 0° C., and then add 37% HCl aqueous solution until the PH value reaches 1. Extract aqueous phase with methyl tertiary butyl ether, wash with sodium carbonate solution three times after the organic phase is separated, extract the excessive o-xylene to obtain red oily crude product under the condition of decompression after the anhydrous sodium sulfate is dried, and use the rapid chromatography method to further purify (silica gel; n-hexane/acetic ether gradient solvent system) 38 g of the mixture of products 2,3- and 3,4-isomers as shown in formula (II-1). (II-1) Analytic data of compound: 1H NMR (methine chemical shift 4.8) MS (m/z: 380.20),

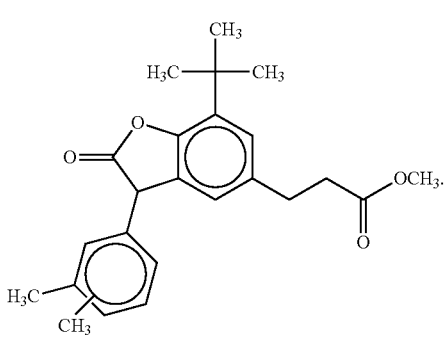

(II-1)

Example 2

Preparation of the mixture of 6-methylheptyl 3-(7-(tert-butyl)-3-(2,3-dimethylphenyl)-2-oxo-2,3-dihydrobenzofuran-5-yl)propanoate and 6-methylheptyl 3-(7-(tert-butyl)-3-(3,4-dimethylphenyl)-2-oxo-2,3-dihydrobenzofuran-5-yl)propanoate In a 1000 mL four-neck round-bottom flask equipped with mechanical stirrer, heat controller and reflux condenser, mix 140 g (0.4 mol) of the product prepared according to the formula (II-1) in Example 1, and 104 g of isooctanol (0.8 mol of EXXAL8 isooctyl alcohol of ExxonMobil Chemical), 40 g of methylbenzene and 2 g of aluminum isopropoxide. Stir the reaction mixture and heat to 85° C. at the nitrogen environment for 5 hours. When the reaction is completed, add 8.8 g of citric acid aqueous solution (50%), stir for 20 minutes continuously, and then add 180 g of water at 75° C. and stir for 20 minutes. Separate the organic phase, then wash with saline twice, and then dry with sodium sulfate. Extract the methylbenzene and excessive isooctanol from the organic phase under the condition of depression, vacuum dry the residues (2 mb, 60° C.) and obtain 188 g of light yellow viscous liquid such as compound (II) in formula I, which is the mixture of 2,3-isomer and 3,4-isomer. Formula (I-1) Analytic data of compound: MS (m/z: 478.31), 1H NMR (methine chemical shift 4.8),

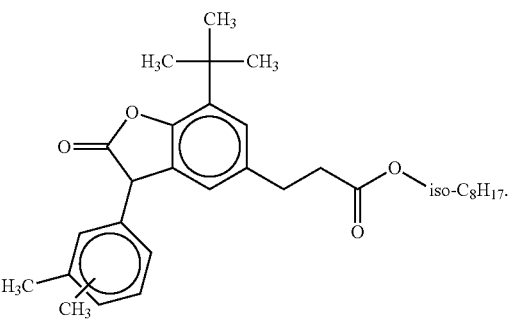

Example 3

Preparation of the mixture of octyl 3-(7-(tert-butyl)-3-(2,3-dimethylphenyl)-2-oxo-2,3-dihydrobenzofuran-5-yl)propanoate and octyl 3-(7-(tert-butyl)-3-(3,4-dimethylphenyl)-2-oxo-2,3-dihydrobenzofuran-5-yl)propanoate.

The preparation method is basically the same with Example 2, and the difference lies in that the n-octyl alcohol is used to replace the isooctanol in Example 2. The 180 g compound (I-2) obtained from separation is the light yellow viscous liquid. Formula (I-2) Analytic data of compound: MS (m/z: 478.31), 1H NMR (methine chemical shift 4.8),

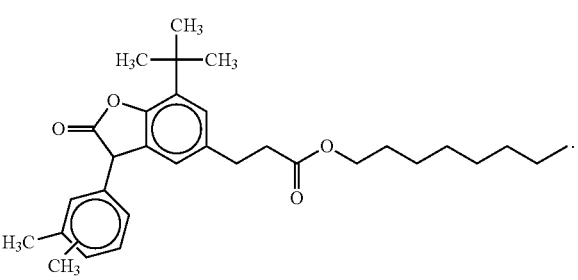

Example 4

Preparation of the mixture of 2-ethylhexyl-3-(7-tert-butyl-3-(2,3-dimethylphenyl)-2-oxo-2,3-dihydrobenzofuran-5-yl)propanoate and 2-ethylhexyl 3-(7-tert-butyl-3-(3,4-dimethylphenyl)-2-oxo-2,3-dihydrobenzofuran-5-yl) propanoate.

The preparation method is basically the same with Example 2, and the difference lies in that the ethylhexyl alcohol is used to replace the isooctanol in Example 2. The 178 g compound (I-3) obtained from separation is the light yellow viscous liquid. Analytic data of compound in formula (I-3): MS (m/z: 478.31), 1H NMR (methine chemical shift 4.8),

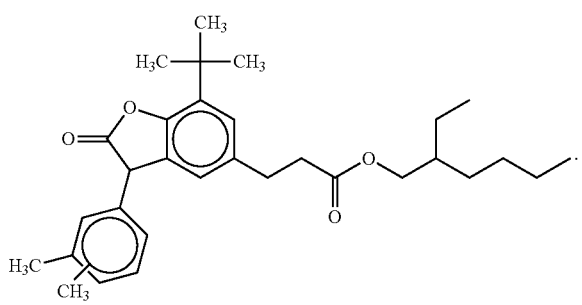

(I-3)

Example 5

Preparation of the mixture of octadecyl 3-(7-tert-butyl-3-(2,3-dimethylphenyl)-2-oxo-2,3-dihydrobenzofuran-5-yl) propanoate and octadecyl 3-(7-tert-butyl-3-(3,4-dimethylphenyl)-2-oxo-2,3-dihydrobenzofuran-5-yl) propanoate.

The preparation method is basically the same with Example 2, and the difference lies in that the propionic acid octadecyl ester is used to replace the isooctanol in Example 2. Obtain 190 g of compound (I-4), separate it and use methanol for recrystallization, and obtain white crystalline powder. Formula I-4 analytic data of compound: MS (m/z: 618.46), 1H NMR (methine chemical shift 4.8),

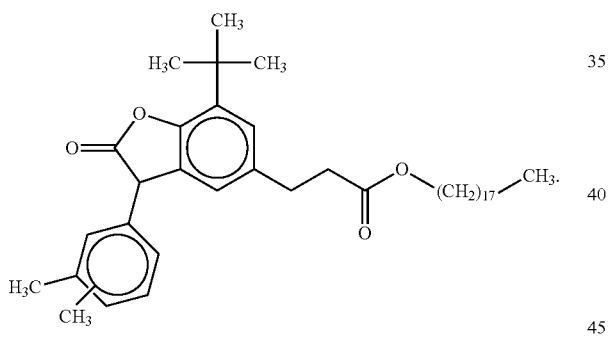

(I-4)

Thermostability of Polyether Polyol

Example 6

The resistance to oxidation of polyether polyol samples is determined through differential scanning calorimetry (DSC). The initial temperature of sample heating is 50° C.; with the presence of oxygen, the temperature elevation rate is 5° C./min until 200° C. is reached. The appearance of exothermic peak means the start of thermal oxidation and attention should be paid to the initial temperature of exothermic peak. A sample with a good thermostability is characterized by the possession of a relatively high initial temperature of thermal oxidation.

Arcol F-3022 (Bayer trade name) is a multifunctional polyether polyol with a hydroxyl value of 56 mg KOH/g, moisture of less than 0.1%, and an acid value of less than 0.04 mg KOH/g.

Irganox 1135 (Bayer trade name) is a kind of liquid phenolic antioxygen with its component of 3-(3,5-ditert-butyl-4-hydroxyphenyl) propionic acid isooctyl ester.

Irganox 5057 (BASF trade name) is a kind of amine antioxidant, a mixture obtained from the reaction from diphenylamine and diisobutylene. Comprising:
a) ≤5% diphenylamine;
b) 8 to 15% 4-butyl diphenylamine;
c) 24 to 32% compound of the following components:
i) 4-tert-octyl diphenylamine,
Ii) 4,4'-2-tert-butyl diphenylamine,
Iii) 2,4,4'-3-tert-butyl diphenylamine;
d) 23 to 34% compound of the following components:
i) 4-tert-octyl-4'-tert-octyl diphenylamine,
ii) ortho, ortho'-, meta, meta', - or dyad, dyad'-2-tert-octyl diphenylamine,
iii) 2,4-tert-butyl-4'; -tert-octyl diphenylamine
e) 21 to 34% compound of the following components:
i) 4,4-2-tert-octyl diphenylamine,
ii) 2,4-tert-octyl-4'; -tert-butyl diphenylamine.

Irganox HP 136 (BASF trade name) is a 3-aryl-benzofuranone antioxidant and its component is the mixture of 5,7-di-tert-butyl-3 (3,4-dimethyl phenyl)-3H-benzofuran-2-ketone and 5,7-di-tert-butyl-3-(2,3, -dimethyl phenyl)-3H-benzfuran-2-ketone.

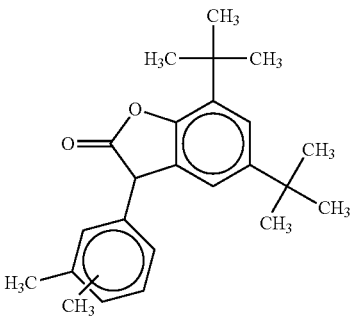

Irganox HP 136

Table 1 shows the mixture of 100 portions of Arcol F-3022 polyether polyol and stabilizer composition

TABLE 1

| Example | Testing samples | Initial temperature of thermal oxidation [° C.] |
|---|---|---|
| Examples 6-1 | 100 portions of polyether polyol, without any additive added. | 134 |
| Example 6-2 | 100 portions of polyether polyol, and a stabilizer composition, comprising 0.32 portion of Irganox 1135, 0.10 portion of Irganox 5057 and 0.03 portion of Irganox HP 136. | 189 |
| Examples 6-3 | 100 portions of polyether polyol, and a stabilizer composition, comprising 0.32 portion of Irganox 1135, 0.10 portion of Irganox 5057 and 0.03 portion of stable compound as shown in formula (I-1). | 196 |
| Examples 6-4 | 100 portions of polyether polyol, and a stabilizer composition, comprising 0.32 portion of Irganox 1135, 0.10 portion of Irganox 5057 and 0.03 portion of stable compound as shown in formula (I-2). | 193 |

TABLE 1-continued

| Example | Testing samples | Initial temperature of thermal oxidation [° C.] |
|---|---|---|
| Examples 6-5 | 100 portions of polyether polyol, and a stabilizer composition, comprising 0.32 portion of Irganox 1135, 0.10 portion of Irganox 5057 and 0.03 portion of stable compound as shown in formula (I-3). | 193 |

Thermostability of Polyether Polyol Containing Fire Retardant

Example 7

The resistance to oxidation of polyether polyol samples is determined through differential scanning calorimetry (DSC) according to the method in Example 6.

FYROL FR-2 LV (ICL trade name) is an additive and liquid fire retardant that contains 3-(1,3-dichlone-2-propyl phosphate ester) commercially uses soft and hard polyurethane foams.

Table 2 shows the mixture of 100 portions of Arcol F-3022 FYROL polyether polyol, FYROL FR-2 LV liquid fire retardant (based on 100 weight portions of polyether polyol) and stabilizer composition (based on 100 weight portions of polyether polyol).

TABLE 2

| Example | Testing samples | Initial temperature of thermal oxidation [° C.] |
|---|---|---|
| Examples 7-1 | 100 portions of polyether polyol, without the addition of FYROL FR-2 LV and any stabilizer. | 134 |
| Examples 7-2 | 100 portions of polyether polyol and 16 portions of FYROL FR-2 LV, without the addition of any stabilizer. | 129 |
| Examples 7-3 | 100 potions of polyether polyol, 16 portions of FYROL FR-2 LV, and a stabilizer composition comprising 0.32 portion of Irganox 1135, 0.10 portion of Irganox5057 and 0.03 portion of Irganox HP136. | 189 |
| Examples 7-4 | 100 portions of polyether polyol, 16 portions of FYROL FR-2 LV, and a composition comprising 0.32 portion of Irganox 1135, 0.10 portion of Irganox 5057 and 0.03 portion of the stabilizer as shown in formula (II-1). | 196 |
| Examples 7-5 | 100 portions of polyether polyol, 16 portions of FYROL FR-2 LV, and a composition comprising 0.32 portion of Irganox 1135, 0.10 portion of Irganox 5057 and 0.03 portion of the stabilizer as shown in formula (II-2). | 193 |
| Examples 7-6 | 100 portions of polyether polyol, 16 portions of FYROL FR-2 LV, and a composition comprising 0.32 portion of Irganox 1135, 0.10 portion of Irganox 5057 and 0.03 portion of the stabilizer as shown in formula (II-3). | 193 |

Thermostability of Polyether/Polyurethane Soft Foams (Resistance to Burning)

Example 8

The resistance to burning is determined through static heat deterioration (static aluminium block test) The foaming blocks are cut into thin tubes (2 cm thick, with a diameter of 1.5 cm). As for each foaming block, the thin tube is the foam sample. Put the foam sample into the aluminium block and heat it.

Maintain the status at 180, 190, 200 and 210° C. for 30 minutes. Resistance to burning is evaluated through the measurement of the colors after the foam samples have heat aging. The measured color value is recorded according to the yellowness index (YI) measured on the foam sample using the ASTM 1926-70 yellowness testing method. A low YI value means a low discoloration, and a high YI value means the severe discoloration of samples. A high whiteness in the foam sample means a better thermostability of foam sample.

Dissolve the stabilizer composition (on the basis of 100 weight portions of polyether polyol) as in Table 3 in the 150.8 g of Arcol F-3022. Add 9.8 g of solution comprising 1.8 g of TEGOSTAB BF 2370 (Evonik trade name; surface activator based on the polysiloxane) and 0.2 g of Tegoamin 33 (Evonik trade name; gelatinized catalytic agent based on triethylenediamine), add 7.8 g of deionized water, and intensely stir this reaction mixture for 15 seconds. Then add 0.3 g of Kosmos 29 (Evonik trade name; the catalytic agent based on stannous octoate), and intensely stir this reaction mixture for 20 seconds continuously. Add 92.2 g of the solution in Demodur T80 (Bayer trade name, mixture of methylbenzene-2,4- and methylbenzene-2,6-diisocyanate), and stir it for 10 seconds continuously. Pour the mixture into a 20×20×20 cm box, and an increase in temperature means that the foaming and heat release should be happening. Cool the foaming blocks and maintain the status at room temperature for 24 hours. All the prepared foaming blocks display the initial white of the corresponding degrees.

TABLE 3

| Example | Testing samples | Yellowness index (YI) Exposed at 180° C. for 30 minutes | Yellowness index (YI) Exposed at 190° C. for 30 minutes | Yellowness index (YI) Exposed at 200° C. for 30 minutes | Yellowness index (YI) Exposed at 210° C. for 30 minutes |
|---|---|---|---|---|---|
| Examples 8-1 | 100 portions of polyether polyol, without any additive added. | 19.3 | 24.9 | 45.6 | 53.9 |

TABLE 3-continued

| Example | Testing samples | Yellowness index (YI) Exposed at 180° C. for 30 minutes | Yellowness index (YI) Exposed at 190° C. for 30 minutes | Yellowness index (YI) Exposed at 200° C. for 30 minutes | Yellowness index (YI) Exposed at 210° C. for 30 minutes |
|---|---|---|---|---|---|
| Examples 8-2 | 100 portions of polyether polyol, and a kind of stabilizer composition, comprising 0.32 portion of Irganox 1135, 0.10 portion of Irganox 5057 and 0.03 portion of Irganox HP 136. | −0.9 | −2.1 | 4.2 | 25.1 |
| Examples 8-3 | 100 portions of polyether polyol, and a kind of stabilizer composition, comprising 0.32 portion of Irganox 1135, 0.10 portion of Irganox 5057 and 0.03 portion of stable compound as shown in formula (I-1). | −1.3 | −2.5 | 3.6 | 23.8 |
| Examples 8-4 | 100 portions of polyether polyol, and a kind of stabilizer composition, comprising 0.32 portion of Irganox 1135, 0.10 portion of Irganox 5057 and 0.03 portion of stable compound as shown in formula (I-2). | −1.3 | −2.3 | 3.8 | 24.2 |
| Examples 8-5 | 100 portions of polyether polyol, and a kind of stabilizer composition, comprising 0.32 portion of Irganox 1135, 0.10 portion of Irganox 5057 and 0.03 portion of stable compound as shown in formula (I-3). | −1.3 | −2.5 | 3.8 | 24.0 |

Thermostability of Fire Retardant Containing Polyether/Polyurethane Soft Foams (Anti-Scorching)

Example 9

The test of anti-scorching is based on the method described in Example 8.

Dissolve 6.8 g of stabilizer composition (0.45 portion, with 100 portions of polyether polyol) as shown in Table 4 into the 150.8 g of Arcol F-3022. Add 24.1 g of FYROL FR-2 LV (16 portions, on the basis of 100 weight portions of polyether polyol), and 9.8 g of solution comprising 1.8 g of TEGOSTAB BF 2370 (Evonik trade name; surface activator based on the polysiloxane) and 0.2 g of Tegoamin 33 (Evonik trade name; gelatinized catalytic agent based on triethylenediamine), add 7.8 g of deionized water, and intensely stir this reaction mixture for 15 seconds. Then add 0.3 g of Kosmos 29 (RTM Evonic; the catalytic agent based on stannous octoate), and intensely stir this reaction mixture for 20 seconds continuously. Add 92.2 g of the solution in Demodur T80 (Bayer trade name, mixture of methylbenzene-2,4- and methylbenzene-2,6-diisocyanate), and stir it for 10 seconds continuously. Pour the mixture into a 20×20×20 cm box, and an increase in temperature means that the foaming and heat release should be happening. Cool the foaming blocks and maintain the status at room temperature for 24 hours. All the prepared foaming blocks display the initial white of the corresponding degrees.

TABLE 4

| Example | Testing samples | Yellowness index (YI) Exposed at 180° C. for 30 minutes | Yellowness index (YI) Exposed at 190° C. for 30 minutes | Yellowness index (YI) Exposed at 200° C. for 30 minutes | Yellowness index (YI) Exposed at 180° C. for 210 minutes |
|---|---|---|---|---|---|
| Example 9-1 | 100 portions of polyether polyol, without any additive added. | 35.2 | 48.1 | 59.9 | 68.5 |
| Example 9-2 | 100 portions of polyether polyol, and a kind of stabilizer composition, comprising 0.32 portion of Irganox 1135, 0.10 portion of Irganox 5057 and 0.03 portion of Irganox HP 136. | 3.7 | 11.7 | 35.9 | 58.2 |
| Example 9-3 | 100 portions of polyether polyol, and a kind of stabilizer composition, comprising 0.32 | 2.1 | 9.2 | 30.6 | 52.8 |

TABLE 4-continued

| Example | Testing samples | Yellowness index (YI) Exposed at 180° C. for 30 minutes | Yellowness index (YI) Exposed at 190° C. for 30 minutes | Yellowness index (YI) Exposed at 200° C. for 30 minutes | Yellowness index (YI) Exposed at 180° C. for 210 minutes |
|---|---|---|---|---|---|
| | portion of Irganox 1135, 0.10 portion of Irganox 5057 and 0.03 portion of stable compound as shown in formula (I-1). | | | | |
| Example 9-4 | 100 portions of polyether polyol, and a kind of stabilizer composition, comprising 0.32 portion of Irganox 1135, 0.10 portion of Irganox 5057 and 0.03 portion of stable compound as shown in formula (I-2). | 2.1 | 9.3 | 30.9 | 53.4 |
| Example 9-5 | 100 portions of polyether polyol, and a kind of stabilizer composition, comprising 0.32 portion of Irganox 1135, 0.10 portion of Irganox 5057 and 0.03 portion of stable compound as shown in formula (I-3). | 2.1 | 9.2 | 30.8 | 53.2 |

Thermostability of ABS (Acrylonitrile-Butadiene-Styrene)

Example 10

Irganox 1076 (Bayer trade name) is a kind of phenolic antioxidant, which contains n-octadecane 3-(3,5-ditert-butyl-4-hydroxyphenyl) propionate. Irgafos 168 (BASF trade name) is a phosphite ester antioxidant that contains 3-(2,4-ditert-butylphenyl) phosphite ester.

100 portions of polymer (comprising 33.3 portions of ABS graft polymer and 66.7 portions of SAS polymer), 1.05 portion of N,N'-ethylene-bis-stearic amide [relative to 100 portions of polymers] and one stabilizer composition according to Table 5 (on the basis of 100 portions of polymer) are mixed in a roller mixing machine for 15 hours. Then, compound the obtained dry mixture in a double-screwed extruder (at 220° C., 110 r and 12 kg/hour). After drying at 80° C. for 3 hours, perform injection molding at 240° C. (machine circulation time: 35.8 seconds; injection speed: 25 mm/second, mold temperature: 60° C.), and obtain the natural ABS test piece with a dimension of 67×64×2 mm.

Measure the initial color of these test pieces, then perform acceleration anti-weathering steel 1000-hour test on the test pieces using the Weather-O-Meter at the following conditions: 340 nm, 0.35 W/m²; internal and external filters of borosilicate; black panel temperature; 63° C.; dark free stage; relative humidity 60%, dry circulation (no rain). Determine the yellowness index (YI) according to DIN 6167. A low YI value means a low discoloration, and a high YI value means the severe discoloration of test pieces. A low discoloration means an effective thermal stability.

TABLE 5

| Example | Testing samples | Yellowness index (YI) |
|---|---|---|
| Examples 10-1 | 100 portions of polymers, without any additive added. | >100 |

TABLE 5-continued

| Example | Testing samples | Yellowness index (YI) |
|---|---|---|
| Examples 10-2 | 100 portions of polymers, comprising 0.057 portion of Irganox 1076, 0.113 portion of Irganos 168 and 0.03 portion of Irganox HP 136. | 50.8 |
| Examples 10-3 | 100 portions of polyether polyol, and a kind of stabilizer composition, comprising 0.057 portion of Irganox 1076, 0.113 portion of Irganos 168 and 0.03 portion of stable compound as shown in formula (I-4). | 46.8 |

According to an embodiment of the present invention that has been described, it should be understood that the above embodiments of the present invention are not limited in any way, and any use or equivalent conversion method equivalents acquired technology solutions are within the scope of the invention as inside.

What is claimed is:
1. A composition comprising:
   component (a): at least one organic materials susceptible to oxidation, heat and/or light-induced degradation; and
   component (b): at least one 3-aryl-benzofuranone compound represented by Formula (I),

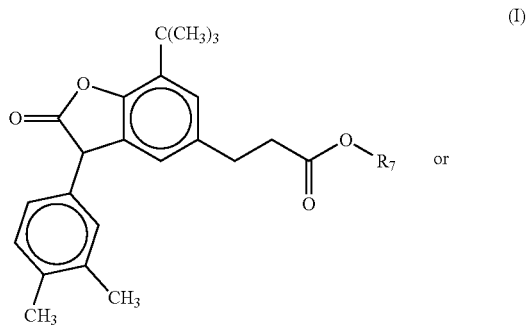

-continued

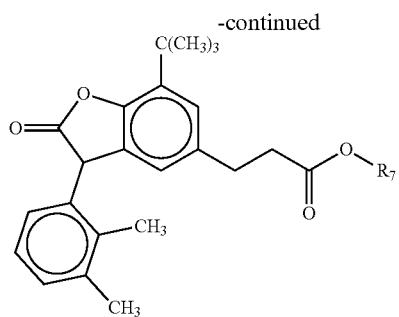

wherein, $R_7$ is $C_7$-$C_9$ or $C_{13}$-$C_{16}$ or $C_{18}$ alkyl.

2. The composition according to claim 1, wherein, the organic material is natural organic polymer, semi-synthetic organic polymer or synthetic organic polymer.

3. The composition according to claim 1, further comprising at least one other additive selected from the group consisting of phenolic antioxidant, phosphite ester or phosphinate ester, amine antioxidant, light stabilizer, acid-scavenger, anti-hydrolytic reagent, processing stabilizer and flame retardant, wherein a weight ratio of said one other additive to the component (b) is 10:1-1:20.

4. A method of the preparation of the 3-aryl-benzofuranone compound in claim 1, comprising the following steps: reacting $C_7$-$C_9$, $C_{13}$-$C_{16}$ or $C_{18}$ alkanols or a mixture thereof with a compound represented by Formula (II) at 5-200° C., using acid catalyst in a solvent or solvents without hydroxyl group,

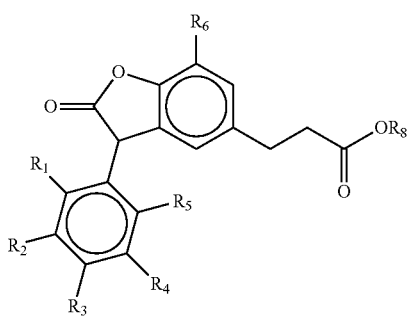

(II)

wherein $R_1$ and $R_2$ are H, $R_3$ and $R_5$ are H or methyl, with the proviso that at least one of $R_3$ and $R_5$ is methyl, $R_4$ is methyl, $R_6$ is 1,1-dimethylethyl, $R_8$ is methyl, and a ratio of said alkanols to said compound represented by Formula (II) is 1-10:1.

5. The composition according to claim 1, wherein, $R_7$ is $C_7$-$C_9$ or $C_{18}$ alkyl.

6. The composition according to claim 1, wherein, $R_7$ is octyl or 2-ethylhexyl or 6-methyl heptyl.

* * * * *